United States Patent [19]

Kohayakawa

[11] Patent Number: 5,675,399
[45] Date of Patent: Oct. 7, 1997

[54] OPHTHALMIC APPARATUS

[75] Inventor: Yoshimi Kohayakawa, Yokohama, Japan

[73] Assignee: Canon Kabushiki Kaisha, Tokyo, Japan

[21] Appl. No.: 429,641

[22] Filed: Apr. 27, 1995

[30] Foreign Application Priority Data

Apr. 30, 1994 [JP] Japan .................... 6-113789
Aug. 30, 1994 [JP] Japan .................... 6-228840

[51] Int. Cl.$^6$ ............................. A61B 3/02
[52] U.S. Cl. ............................. 351/237; 351/222
[58] Field of Search ............... 351/239, 243, 351/240, 237, 246, 222, 223

[56] References Cited

U.S. PATENT DOCUMENTS

| | | | |
|---|---|---|---|
| 4,105,302 | 8/1978 | Tate, Jr. .................... | 351/239 |
| 4,293,198 | 10/1981 | Kohayakawa et al. . | |
| 4,609,287 | 9/1986 | Kohayakawa .................... | 356/124 |
| 4,820,037 | 4/1989 | Kohayakawa et al. . | |
| 5,144,346 | 9/1992 | Nakamura et al. .................... | 351/208 |
| 5,231,430 | 7/1993 | Kohayakawa .................... | 351/243 |
| 5,237,351 | 8/1993 | Kohayakawa et al. .................... | 351/243 |
| 5,249,003 | 9/1993 | Kohayakawa .................... | 351/211 |
| 5,420,650 | 5/1995 | Kohayakawa .................... | 351/206 |

*Primary Examiner*—Hung X. Dang
*Attorney, Agent, or Firm*—Fitzpatrick, Cella, Harper & Scinto

[57] ABSTRACT

An ophthalmic apparatus includes a visual target indicating portion for indicating patterns of at least three directions each consisting of a plurality of parallel lines, a visual target optical system for making variable a diopter of the pattern presented to an examinee, and a response inputting device for inputting a response of the examinee. A refractive power of an eye of the examinee is obtained from a diopter of the pattern at the time the examinee inputs a response thereof through the response inputting device at the limit of his visual recognition of the pattern. In another arrangement, a refractive power of an eye of the examinee is obtained from intervals of the parallel lines at the time the examinee inputs a response thereof through the response inputting device at the limit of visual recognition of the pattern, the intervals of the parallel lines of which change over time.

12 Claims, 4 Drawing Sheets

OPHTHALMIC APPARATUS

BACKGROUND OF THE INVENTION

1. Field of the Invention

The present invention relates to an ophthalmic apparatus used in measuring the eye refractive power of people at ophthalmic hospitals or spectacles shops.

2. Related Background Art

For subjective measurement of the eye refractive power, conventional technology employed a method, using a unit to be viewed by indicating a visual target for an examined eye using lenses with different refractive powers like a phoropter, for measuring the eye's refractive power in combination with optotypes, or a method for measuring the eye's refractive power by putting a provisional frame for spectacles on an examinee and successively setting interchangeable lenses with different refractive powers on and off the provisional frame. Used in some cases is a subjective refractive-power measuring apparatus which is arranged in such a manner that a turret type subjective refractometer is incorporated in a housing and an examiner controls the refractometer while the examinee is looking into an observation window.

However since the measurement of refractive power is carried out based on examiner's judgment, either one of the above conventional examples, requires an examiner capable of making the judgment. Further, the apparatus requires the use of a special optical member such as a cylindrical lens.

SUMMARY OF THE INVENTION

A first object of the present invention is to provide an ophthalmic apparatus which has solved the above problem, which obviates the need for a special optical member, and which can measure the eye's refractive power using a device controlled"; and by the examinee himself or herself.

The other objects of the present invention will become apparent in the following description of embodiments.

DESCRIPTION OF THE PREFERRED EMBODIMENTS

The present invention will be described in detail based on the embodiments shown in the accompanying drawings.

Figure 1:
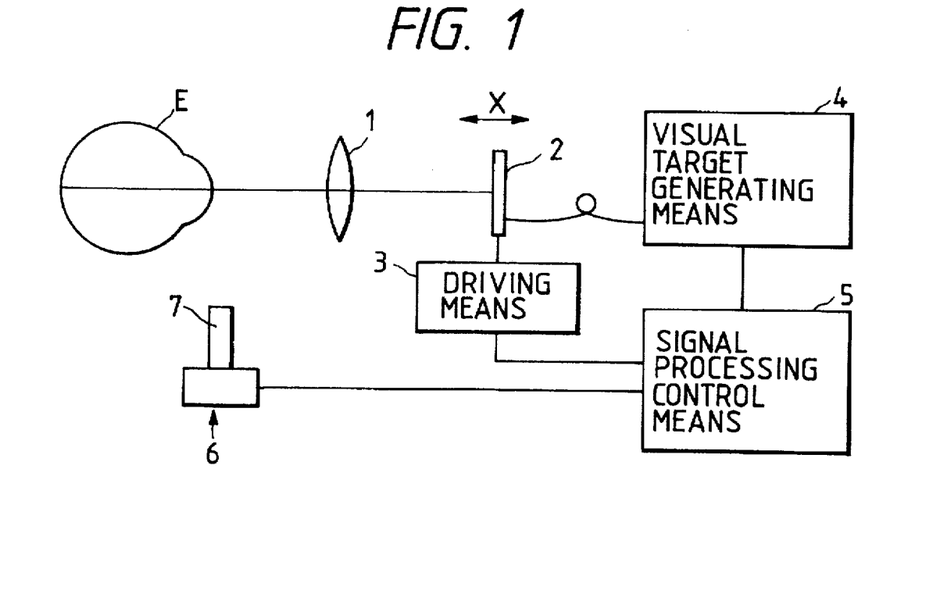
FIG. 1 is a structural drawing of a first embodiment.
Figure 2A:
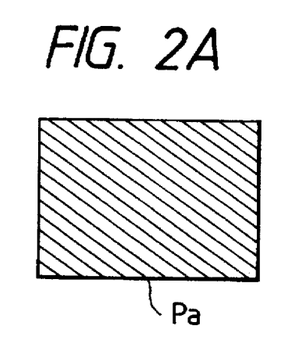
FIGS. 2A, 2B, and 2C are explanatory drawings of stripe patterns in a visual target.
Figure 2B:
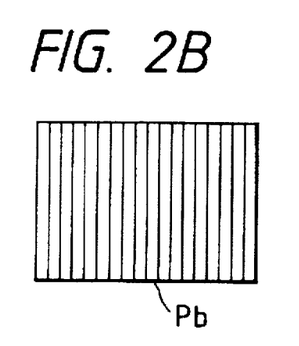
Figure 2C:
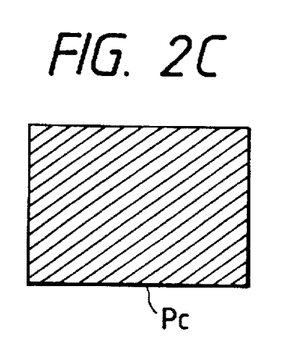

FIG. 1 is a structural drawing of the first embodiment, in which a lens 1, and a visual target 2 consisting of a liquid crystal display panel for displaying an image are arranged on an optical path in front of an examined eye E. The examined eye E is located at a front focal point position of lens 1, so that it is kept so as not to change its visual angle even if the visual target 2 moves. The visual target 2 is connected to driving means 3, which drives it in the direction of the arrow X on the optical axis in order to change its diopter. Further, the apparatus is provided with visual target generating means 4 for generating stripe patterns Pa, Pb, Pc of at least three directions as shown in FIGS. 2A, 2B, and 2C. Instead of using the liquid crystal display means as the visual target 2, the visual target may be a screen on which a one-directional stripe pattern is written and which is arranged to be mechanically rotated so as to match either one of three directions.

Figure 3:
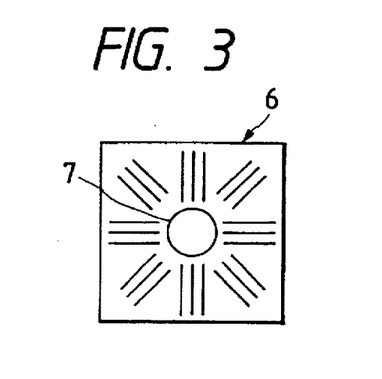
FIG. 3 is a plan view of responding means.

An output terminal of signal processing control means 5 is connected to each of the driving means 3 and the visual target generating means 4, and responding means 6 with which an examinee gives a response when visually recognizing the visual target 2 is connected to the signal processing control means 5. The responding means 6 is provided with a control rod 7, through which the examinee can give a response of either direction of a visually recognized pattern out of the stripe patterns Pa, Pb, Pc, which are the three-directional stripe patterns written around the control rod 7 as shown in FIG. 3.

Upon measurement, either one of the stripe patterns Pa, Pb, Pc as shown in FIGS. 2A, 2B and 2C is indicated on the visual target 2 by the visual target generating means 4, and the examinee observes the displayed visual target 2. The driving means 3 drives the visual target 2 in the X direction to change its diopter, and when visually recognizing it, the examinee responds by bringing the control rod 7 down in a direction of a same stripe pattern on the responding means 6. The responding means 6 may be constructed in such an arrangement that the examinee can respond by simply pressing a button when visually recognizing the target, instead of inputting the direction of the stripe pattern.

After the signal processing control means 5 detects a signal from the responding means 6, it controls the diopters of the displayed pattern in the same manner while indicating another stripe pattern with a different direction and pitch of stripes, and calculates the target diopter of the next pattern from the target diopter at the time of response by the examinee.

The visual target 2 is moved from afar to near for obtaining a far-point refraction value, while it is moved in the opposite direction from near to far, for obtaining a near-point refraction value. Namely, if the visual target 2 is moved from the far side of plus diopters, for example +20 diopter, to the near side, the examinee can visually recognize the visual target 2 when the visual target 2 reaches a position of the examinee's eye refraction value of a meridian normal to the stripe pattern, and responds at that time. In the opposite case, the examinee gives this response when the examinee becomes incapable of visually recognizing the visual target 2.

Visual acuity is determined from the response of the examinee's recognition when the stripe patterns, changing their pitches from fine to coarse, are indicated. The finer the pitch of the stripe pattern, the more accurate the measurement of the eye's refractive power. Thus, a first measurement is done to obtain an approximate refraction value using a stripe pattern of a relatively wide pitch corresponding to a visual acuity of about 0.5, and then the measurement accuracy is raised, gradually using stripe patterns of finer pitches. In this case, the speed of changing the diopter is faster for stripe patterns of wide pitches, but slower for stripe patterns of fine pitches. The way of thus displaying the stripe patterns in a particular order is preliminarily programmed into the device.

Since refraction values differ depending upon directions of the meridians of stripe patterns in case of the astigmatic eye's, stripe patterns of at least three directions are indicated to obtain refraction values in the directions of three meridians. From those values the signal processing control means 5 calculates refraction values including astigmatism. In this case, regarding a change in refraction value according to meridional direction as sinusoidal, the examinee's eye refraction values consisting a spherical refraction value, a quantity of astigmatism, and the angle of the astigmatism can be obtained.

Figure 4:
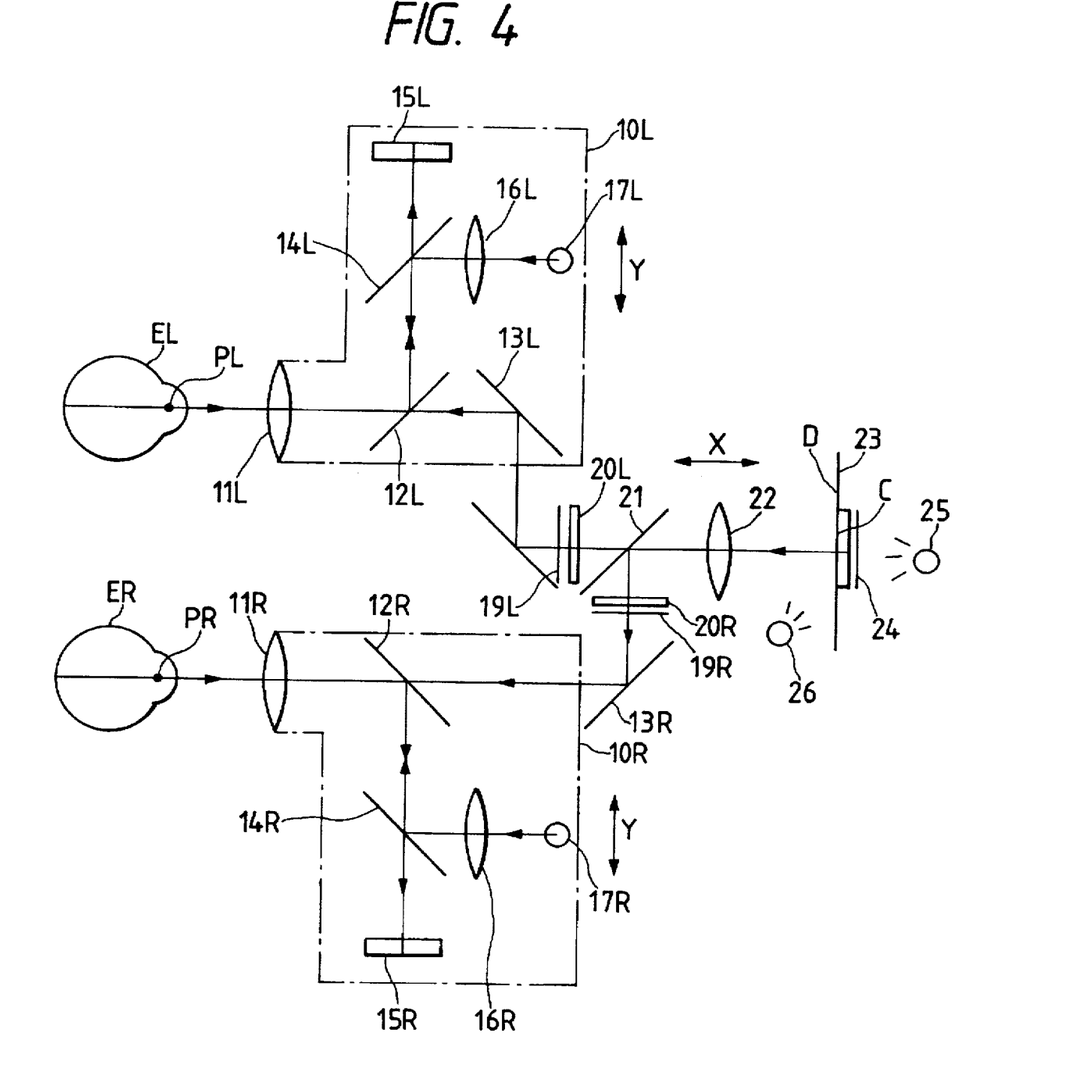
FIG. 4 is a structural drawing of a second embodiment.

FIG. 4 shows the second embodiment and is a structural drawing of a subjective refraction measuring apparatus for measurement under binocular vision, as observed from the top. In front of the left and right eyes EL, ER there are provided units 10L, 10R, each of which can be driven in the directions of arrow Y along the eye width direction. Within each of these units 10L, 10R there are an objective lens 11L, 11R, a dichroic mirror 12L, 12R, and a mirror 13L, 13R, arranged from the examined eye (EL, ER) side. Placed on the reflection side of each dichroic mirror 12L, 12R are a half mirror 14L, 14R and a two-dimensional photoelectric array sensor 15L, 15R, respectively, for measuring the pupil distance, while placed on the entrance side of the half mirror 14L, 14R are a lens 16L, 16R and a light source 17L, 17R, respectively, such as infrared LED.

A mirror 21 is provided on the reflection side of mirror 13L, and a polarizing plate 19L, 19R and a liquid crystal panel 20L, 20R are arranged on the reflection side of the mirror 21 or the mirror 13, respectively. When a voltage is applied to the liquid crystal panel 20L, 20R, its rotary polarization function disappears; when the voltage is cut off, a polarization rotation of 45° appears, whereby stripe patterns of the target C can be indicated alternately, eye by eye, by alternately applying the voltage. A half mirror 21 is located at a position of an intersection between two optical paths behind the liquid crystal panels 20L, 20R. In addition, there are a lens 22 driven in the directions of arrow X, a visual target 23 consisting of a 90° TN liquid crystal panel C for image, and a polarizing plate 24 as arranged on same axis as the polarizing plate 19.

Figure 5:
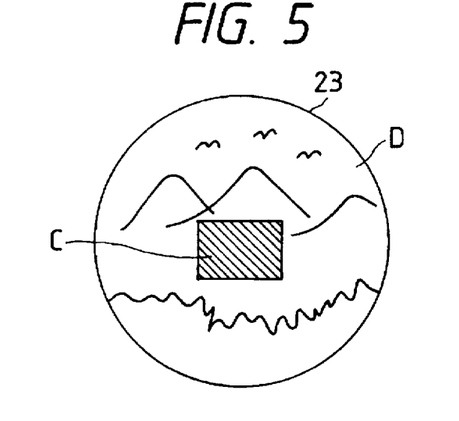
FIG. 5 is a front elevation of a center target and a peripheral visual field.

The visual target 23 is composed, as shown in FIG. 5, of a center visual target C with polarization for indicating stripe patterns of at least three directions, and a peripheral visual field D consisting of a diffuse reflection surface on which a distant view is drawn. Set behind the visual target 23 is a light source 25 for illuminating the center target C from the back, and provided obliquely, ahead of the visual target 23, is a light source 26 for illuminating the peripheral visual field D from obliquely ahead. Although omitted in the drawing in the present embodiment, there are the visual target generating means and responding means provided in the same arrangement as in the first embodiment.

Figure 6:
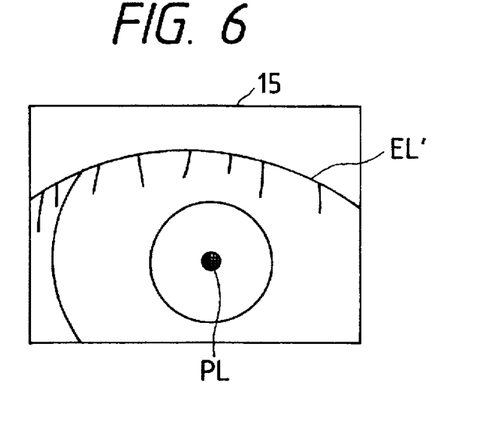
FIG. 6 is an explanatory drawing of an anterior ocular image and a light source image formed on a two-dimensional array sensor.

A light beam from the light source 17L is guided through the lens 16L to be reflected by the half mirror 14L and the dichroic mirror 12L and is once focused at the rear focal point of objective lens 11L. After that, a parallel beam is projected from the objective lens 11L onto the left eye EL of the examinee. Light from source image PL formed on the cornea of the left eye EL returns along the same optical path to pass through the half mirror 14L, and is refocused together with an anterior ocular image EL' on the two-dimensional array sensor 15L, as shown in FIG. 6.

Similarly, for the right eye ER, an image PR of the light source 17R is refocused on the two-dimensional array sensor 15R. The positions of these light source images PL, PR are calculated by a computer to obtain the pupil distance, and the units 10L, 10R are driven in the directions of arrow Y to adjust the pupil distance. A recommended arrangement is such that the adjustment of the pupil distance is started when the apparatus detects an examinee's face approaching the apparatus.

Stripe patterns of at least three directions are indicated in the center target C in the visual target 23, in a similar manner as in the first embodiment, and measurement is successively carried out for every eye while the examinee is in a state of binocular vision. A light beam from the visual target 23 is split into left and right optical paths by the half mirror 21, which reach the left and right eyes EL, ER, respectively. Then the lens 22 is driven in the direction of arrow X on the optical axis, and a refraction value is measured by changing the diopter.

Here, because the visual target 23, different from ordinary liquid crystal display panels or the visual target 2 in the first embodiment, is provided with the polarizing plate 24 only on one side (though FIG. 1 is drawn as omitting the polarizing plates), the examinee becomes capable of observing the stripe pattern through the polarizing plate 19L or 19R having a transmission polarization direction normal to that of the polarizing plate 24. Namely, when a voltage is applied to the liquid crystal panel 20L or 20R, the examinee can observe the stripe pattern, because molecules of liquid crystal are aligned vertically to the surface and show no polarization rotation. Successively applying the voltage in this manner, the stripe patterns can be successively indicated as selecting the left or right eye EL, ER.

In contrast, because the peripheral visual field D illuminated by the light source 26 is the diffuse reflection surface and has no polarization, it can be always observed by the both eyes, irrespective of the operation of liquid crystal panel 20L or 20R. Thus, if image fusion is made as observing the peripheral field D, no convergence occurs under binocular vision, thus causing no accommodation of the examined eye.

Figure 7:
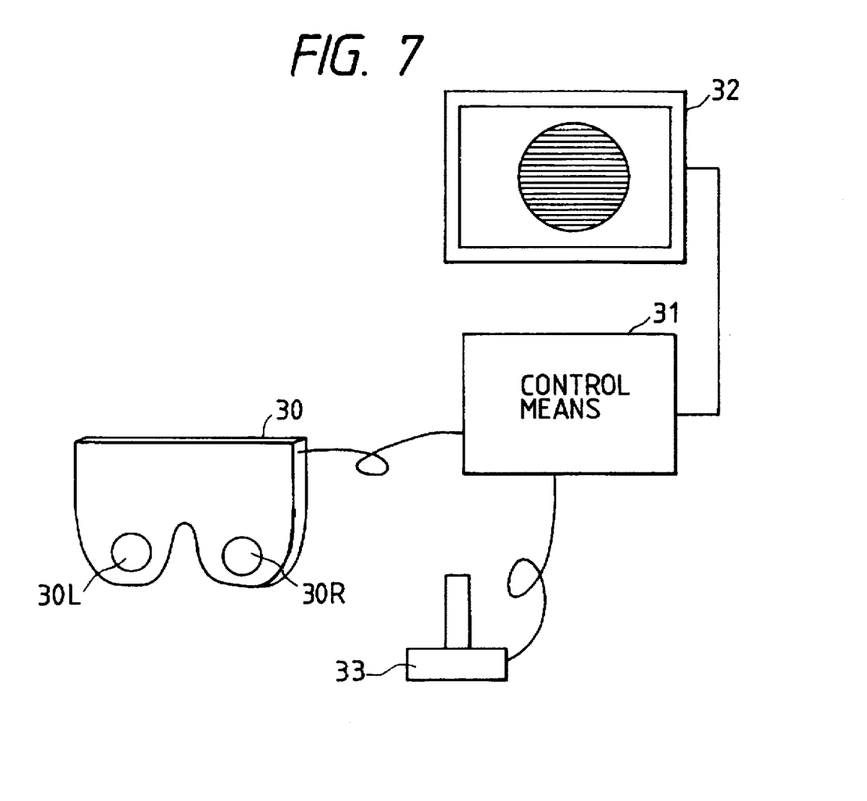
FIG. 7 is a structural drawing of a third embodiment.

FIG. 7 shows the third embodiment, which is a subjective refraction measuring apparatus using a phoropter. A phoropter head 30 includes a lens turret and a drive motor thereof, and openings 30L, 30R for the examinee to look therethrough are perforated through the head. The phoropter head 30 is connected to control means 31 including a visual target pattern generating circuit and a sequence program, and signal terminals of the control means 31 are connected to a television monitor 32 for indicating a generated stripe pattern, and to responding means 33 for the examinee to respond upon visually recognizing the stripe pattern.

The target pattern generating circuit in the control means 31 generates stripe patterns of at least three directions on the television monitor 32 separately from each other, and the examinee observes a stripe pattern on the television monitor 32 located about 5 m apart, through the openings 30L, 30R in the phoropter head 30 and responds through the responding means 33. In this case, according to the stored program, the lenses in the phoropter head 30 are interchanged one by one, based on a signal from the control means 31, to gradually change the diopter of the visual target from the hyperopia side to the myopia side. The examinee gives a response when visually recognizing the pattern, and then a refraction value is obtained from the lens diopter of the phoropter head 30 at this moment. The degree of astigmatism can also be measured by performing successive measurements with the stripe patterns of three directions.

In the subjective refraction measuring apparatus in the embodiments, as described above, the stripe patterns of at least three directions are generated in the visual target and each refraction value is obtained from the lens diopter of the phoropter head 30 at a point of response of the subject. Then, refraction values, including astigmatism, are calculated in control means 31 using the refraction values for the three directions, whereby without especially needing an examiner upon measurement, the examinee himself or herself can perform subjective refraction measurement by easy operation using the simple apparatus.

Figure 8:
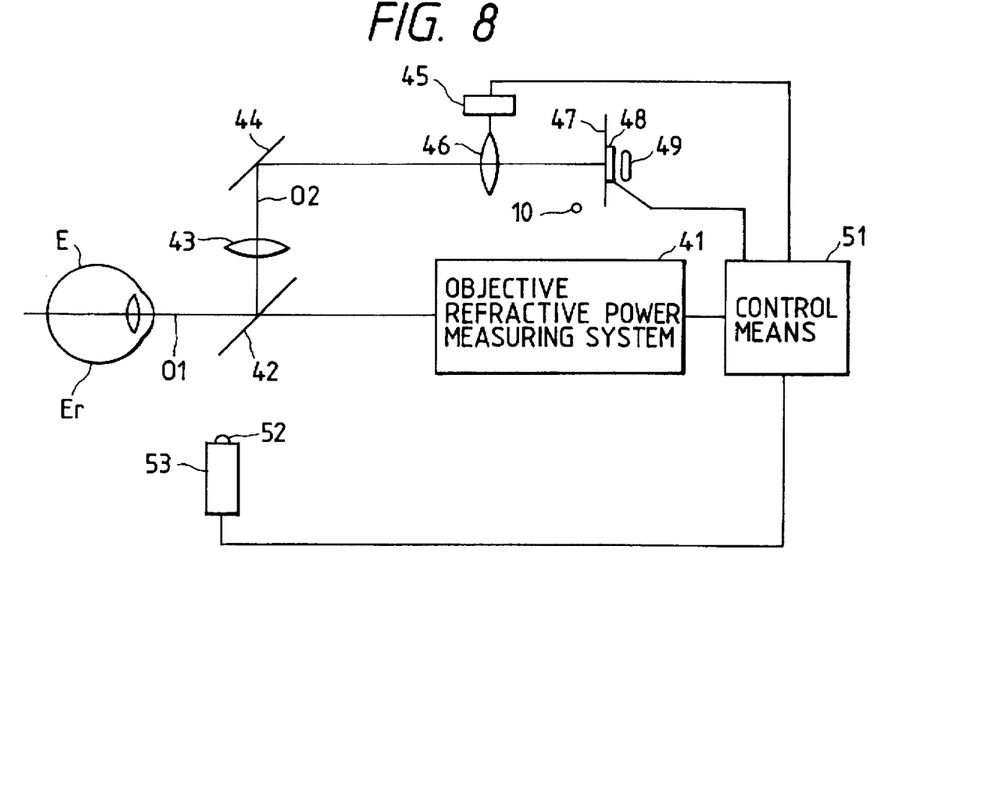
FIG. 8 is a structural drawing of a fourth embodiment.

FIG. 8 is a structural drawing of the fourth embodiment, in which an objective refracting power measuring system 41 is provided on an optical path 01 in the direction along the visual axis of the examined eye E and a light beam splitting member 42 is placed between the objective refractive power measuring system 41 and the examined eye E. Further, arranged in order on an optical path 02 on the reflection side of beam splitting member 42 are a lens 43, a mirror 44, a diopter-variable lens 46 movable along the optical path 02 by drive means 45, a rectangular liquid crystal panel 48 for indication of image, surrounded by a disk, peripheral visual field 47 as shown in FIG. 9, and a light source 49; and a light source 50 is set near the peripheral visual field 47, thus constituting a visual target projection optical system.

Further, in order to control the entire apparatus, the apparatus is provided with control means 51 consisting of a mark generating circuit etc., and the objective refractive power measuring system 41, the drive means 45, the image indication liquid crystal panel 48, and the responding means 53 provided with an input button 52 each are connected to the control means 51.

Figure 9:
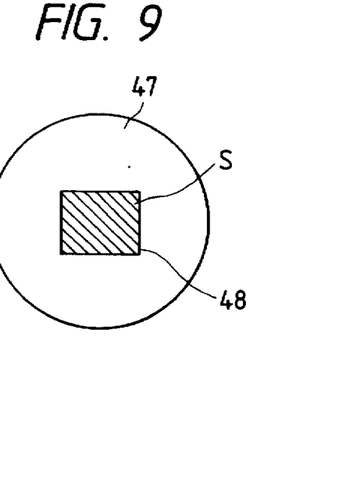
FIG. 9 is a front elevational of a peripheral visual field and a liquid crystal panel for indicating an image.

Here, the peripheral visual field 47 around the image indication liquid crystal panel 48, as shown in FIG. 9, is provided for widening the visual field of the examined eye E for relax accommodation. The peripheral field is made of a material with diffuse reflectivity, and a distant view or the like is drawn thereon.

For subjective refractive power measurement, an objective refractive power is first measured by the objective refracting power measuring system 41. In this case, in order to guide the diopter of the examined eye E to the far side, a distant view target is indicated on the image indication liquid crystal panel 48 generated by the control means 51. Light from the light source 49 illuminates the image indication liquid crystal panel 48 from the back and then passes through the diopter-variable lens 46 to be reflected by the mirror 44 and the beam splitting member 42 and then is projected onto the fundus oculi Er of the examined eye E. Also, the light source 50 illuminates the peripheral visual field 47 from the front. The illumination light is reflected by the peripheral visual field 47 because of its diffuse reflectivity to be guided onto the fundus oculi Er of the examined eye E by the lens 43 and the beam splitting member 42, whereby the distant view target consisting of the peripheral visual field 47 and the image indication liquid crystal panel 48 is indicated for the examined eye E. While the examiner makes the examinee's gaze fixed at a distant view target, the examiner activates the drive means 45 through the control means 51 to move the diopter-variable lens 46 along the optical path 02, thereby changing the diopter of the distant view target and guiding the diopter of the examined eye E to a far point.

After completion of guidance of the diopter, a measuring light source inside the objective refractive power measuring system 41 is turned on. A light beam emitted from the measuring light source passes through the beam splitting member 42 to be projected onto the fundus oculi Er of the examined eye E. A beam of reflected light on the fundus oculi Er returns along the same optical path 01 to be received by light-receiving means inside the objective refractive power measuring system 41, and the computer in the control means 51 calculates the objective refractive power. Since the measurement and calculation of the objective refractive power is well known, a description thereof is omitted herein.

Next, a stripe visual target S consisting of parallel lines is indicated on the image indication liquid crystal panel 48, as shown in FIG. 9, to measure a stripe visual acuity. The control means 51 controls the drive means 45 to move the diopter-variable lens 46, to set the diopter of stripe visual target S according to the objectively measured refractive power in the direction perpendicular to the stripe, and to gradually decrease the pitches of stripe visual target S.

The examiner preliminarily makes the examinee grip the responding means 53, and gives an instruction that the examinee should press the input button 52 when the examinee becomes incapable of visually recognizing the stripe of the stripe visual target S. A signal from the responding means 53 is input into the control means 51 when the input button 52 is depressed, and a stripe visual acuity is obtained, based on pitches of the stripe visual target S at the response, in the control means 51.

In case three stripe targets S in the vertical direction, in the horizontal direction, and in the 45° direction are indicated on the image indication liquid crystal panel 48, whereby stripe visual acuities can be obtained in the directions of three meridians. For example, for measuring a stripe visual acuity in the direction of the vertical meridian, the stripe target S of the horizontal direction is displayed on the image indication liquid crystal panel 48 while the diopter of the stripe visual target S is set according to the objectively measured refractive power of the direction of the vertical meridian. As far as the fundus of the examined eye E is conjugate with the visual target S, the stripe visual acuity changes little depending upon the directions of meridians, and therefore, a stripe visual acuity measured in the one meridian direction may be regarded as a stripe visual acuity in another meridian direction. By making a correlation between stripe visual acuities and visual acuities of Landolt rings etc., a stripe visual acuity can be converted into ordinary visual acuity. This visual acuity represents a corrected visual acuity. It is thus possible to measure corrected visual acuity without using a cylindrical lens for correction of astigmatism.

Finally, a subjective refractive power is measured while indicating a stripe visual target S of a little wider pitches on the image indication liquid crystal panel 48 than the finest pitches for the examinee's eye E which are capable of being visually recognizing.

The control means 51 sets an initial value of diopter of the stripe visual target S to be equal or a little on the myopia side to the objective refractive power in the direction of a corresponding meridian, and then gradually moves the diopter-variable lens 46 to change the diopter of the stripe visual acuity to the hyperopia side. The examinee presses the input button 52 when becoming incapable of visually recognizing the stripe visual target S. Once the input button 52 is depressed, the control means 51 obtains the diopter of the stripe visual target S at this point, which is regarded as the subjective refractive power for the direction. The control means 51 changes the direction of the stripe visual target S as being vertical, horizontal, or 45°, measures respective refractive powers in the directions of three meridians corresponding to these three directions, and obtains subjective refraction values including astigmatism from the refractive powers in these three meridian directions, in the inside of a computer.

In this example the diopter of the stripe visual target S is changed from the myopia side to the hyperopia side, but an alternative modification may be arranged in such a manner that the diopter is changed in the opposite way from the hyperopia side to the myopia side and the examinee depresses the input button 52 when visually recognizing the stripe visual target S. In changing the diopter of stripe target S, the examiner may manually change the diopter by manipulating the control means 51 or it may be automatically changed at a constant rate by the control means 51.

The response of visual recognition of the stripe visual target S is given by the examinee depressing the input button 52, but a modification may be constructed in such an arrangement that the examinee responds to inform the examiner of visual recognition by voice and the examiner depresses the input button 52. Also, the responding means 53 may be arranged to permit input of the direction of stripe visual target S.

The directions of stripe visual targets S were preliminarily determined as the vertical direction, the horizontal direction, and the 45° direction of, but the apparatus may be so arranged that by the stored program in the control means 51, the image indication liquid crystal panel 48 can indicate each of stripe visual targets S in the principal meridian directions obtained from the results of objective refractive power measurement and in an intermediate direction between them.

Figure 10:
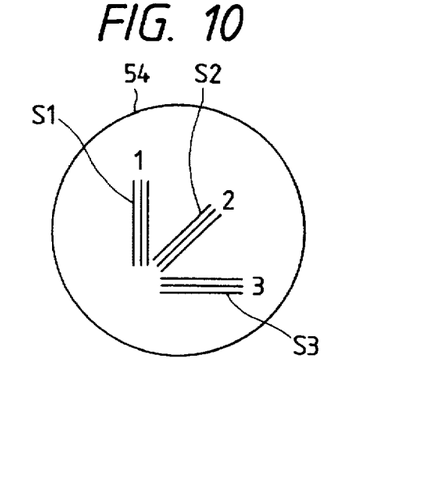
FIG. 10 is a front elevational view of a visual target plate.

Or, instead of changing the directions of stripe targets S by controlling the image indication liquid crystal panel 48, a modification may employ a visual target plate 54 on which visual targets S1 to S3, indicating three directions are preliminarily written as shown in FIG. 10. Since the visual target plate 54 is made from an optically transparent member, the three visual targets S1 to S3 are indicated for the examined eye E when it is illuminated from the back by the light source 49.

These visual targets S1 to S3 each are three parallel lines of pitches of one minute, and the directions of the visual targets are the vertical direction, the 45° direction of, and the horizontal direction, which can be discriminated by numerals "1" to "3".

The examiner designates a visual target S1 to S3 to be responded to upon visual recognition by the numeral "1" to "3". For example, an instruction is such that for measuring a refractive power in the horizontal direction, the examinee is requested to visually recognize the visual target S1 of numeral "1".

The control means 51 matches an initial value of the diopter of visual target S1 to S3 with the objective refractive power preliminarily measured and moves the diopter-variable lens 46 to gradually change the diopter to the hyperopia side, and the examinee depresses the input button 52 when the examinee becomes incapable of observing the stripes in the designated target S1 to S3 in a separate state. The computer inside the control means 51 obtains the diopter of visual target S1 to S3 at the point when the input button 52 is depressed. These values are regarded as subjective refractive powers in the three meridian directions corresponding to the directions of the visual targets S1 to S3 and, based on the thus obtained refractive powers in the three meridian directions, refraction values consisting of an astigmatism quantity, an astigmatism angle, and a spherical degree are calculated.

Since the subjective refractive power measuring apparatus of the embodiments as described above are so arranged that the examinee responds upon visual recognition of a one-dimensional pattern, for example, such as stripes, the examinee can readily give a response to visual recognition. Also, the astigmatism angle and astigmatism degree can be measured by measuring refractive powers in predetermined meridian directions, whereby the astigmatism angle does not have to be measured separately from the refractive power, thereby enabling the subjective refractive power to be measured easily and within a short time. Since the apparatus requires no special optical member, such as a cylindrical lens, in measuring refraction or visual acuity of an astigmatic eye, the structure is simpler.

What is claimed is:

1. An ophthalmic apparatus comprising:
   a visual target indicating portion for indicating patterns of at least three directions each consisting of a plurality of parallel lines to be presented to an examinee;
   a visual target optical system for making variable a diopter of the pattern presented to the examinee; and
   response inputting means for inputting a response of the examinee,
   wherein refractive values of an eye of the examinee are obtained on the basis of the diopter of said visual target optical system at the time the examinee inputs a response through said response inputting means at the limit of visual recognition of the pattern which changes its diopter.

2. The apparatus according to claim 1, wherein said visual target indicating portion generates a stripe pattern as the pattern.

3. The apparatus according to claim 1, wherein said visual target indicating portion indicates the pattern on a liquid crystal display.

4. The apparatus according to claim 1, wherein said visual target indicating portion indicates a stripe pattern in a central portion thereof and a peripheral portion thereof is a diffuse reflection surface.

5. The apparatus according to claim 1, wherein refractive powers in three meridian directions of the eye of the examinee are obtained using indications of patterns in three directions given by said visual target indicating portion.

6. The apparatus according to claim 1, wherein the refractive power of the eye of the examinee is obtained from a diopter at the time of a response of the examinee through said response inputting means when the examinee visually recognizes the pattern.

7. The apparatus according to claim 1, wherein the refractive power of the eye of the examinee is obtained from a diopter at the time of a response of the examinee through said response inputting means when the examinee becomes incapable of visually recognizing the pattern.

8. The apparatus according to claim 1, further comprising a phoropter head for the examinee to look thereinto upon measurement.

9. The apparatus according to claim 1, further comprising means for measuring an eye refractive power of the examinee in an objective manner.

10. The apparatus according to claim 1, further comprising means for changing intervals of the parallel lines in the pattern.

11. An ophthalmic apparatus comprising:
    a visual target indicating portion for indicating patterns of at least three directions each consisting of a plurality of parallel lines to be presented to an examinee;
    a visual target optical system for making variable a diopter of the pattern presented to the examinee;
    response inputting means for inputting a response of the examinee; and
    means for changing the intervals of the parallel lines;
    wherein a refractive power of an eye of the examinee is obtained from intervals of the parallel lines at the time when the examinee inputs a response thereof through said response inputting means at the limit of visual recognition of the pattern, the intervals of the parallel lines of which are changing.

12. An ophthalmic apparatus comprising:
    a visual target indicating portion for indicating patterns of at least three directions each consisting of a plurality of parallel lines to be presented to an examinee;
    a visual target optical system for making variable a diopter of the patterns presented to an examinee;
    means for changing the intervals of the parallel lines; and
    response inputting means for inputting a response of the examinee,
    wherein the visual acuity of the examinee is obtained on the basis of the pitches of the patterns at the time the examinee inputs a response through said response inputting means at the limit of visual recognition of the patterns.

* * * * *

UNITED STATES PATENT AND TRADEMARK OFFICE
CERTIFICATE OF CORRECTION

PATENT NO. : 5,675,399
DATED : October 7, 1997
INVENTOR(S) : YOSHIMI KOHAYAKAWA

It is certified that error appears in the above-identified patent and that said Letters Patent is hereby corrected as shown below:

COLUMN 1:
    Line 11, "method," should read --method--.
    Line 24, "of" should read --of the eye's--.
    Line 35, "controlled"; and " should read --controlled by--.
    Line 46, "elevation" should read --elevational view--.
    Line 54, "elevational" should read --elevational view--.

COLUMN 2
    Line 59, "raised,gradually" should read --raised gradually--.
    Line 66, after "of" (second occurrence) insert --the--; and before "astigmatic" delete "the".
    Line 67, "eye's," should read --eyes,--.

COLUMN 3:
    Line 6, "consisting" should read --consisting of--.
    Line 34, "on" should read --on the--.

UNITED STATES PATENT AND TRADEMARK OFFICE
CERTIFICATE OF CORRECTION

PATENT NO. : 5,675,399
DATED : October 7, 1997
INVENTOR(S) : YOSHIMI KOHAYAKAWA

It is certified that error appears in the above-identified patent and that said Letters Patent is hereby corrected as shown below:

COLUMN 7:
    Line 3, "direction of," should read --direction,--.
    Line 12, "directions" should read --directions,--.
    Line 13, "written" should read --written,--.
    Line 21, "directions of," should read --directions,--.

Signed and Sealed this

Ninth Day of June, 1998

BRUCE LEHMAN

Attest:

Attesting Officer

Commissioner of Patents and Trademarks